United States Patent
Pouchoulin et al.

(10) Patent No.: US 11,992,595 B2
(45) Date of Patent: May 28, 2024

(54) EXTRACORPOREAL BLOOD TREATMENT APPARATUS AND METHOD FOR MONITORING PRESSURES IN AN EXTRACORPOREAL BLOOD TREATMENT APPARATUS

(71) Applicant: GAMBRO LUNDIA AB, Lund (SE)

(72) Inventors: Dominique Pouchoulin, Tramoyes (FR); David Karlsson, Lund (SE)

(73) Assignee: Gambro Lundia AB, Lund (SE)

( * ) Notice: Subject to any disclaimer, the term of this patent is extended or adjusted under 35 U.S.C. 154(b) by 543 days.

(21) Appl. No.: 17/283,749

(22) PCT Filed: Oct. 11, 2019

(86) PCT No.: PCT/EP2019/077662
§ 371 (c)(1),
(2) Date: Apr. 8, 2021

(87) PCT Pub. No.: WO2020/074733
PCT Pub. Date: Apr. 16, 2020

(65) Prior Publication Data
US 2021/0379266 A1   Dec. 9, 2021

(30) Foreign Application Priority Data

Oct. 11, 2018 (EP) .................................... 18199898

(51) Int. Cl.
*A61M 1/36* (2006.01)
(52) U.S. Cl.
CPC ........ *A61M 1/3639* (2013.01); *A61M 1/3623* (2022.05); *A61M 1/3653* (2013.01); *A61M 2205/3331* (2013.01)
(58) Field of Classification Search
CPC .............. A61M 1/3639; A61M 1/3623; A61M 1/3653; A61M 2205/3331;
(Continued)

(56) References Cited

U.S. PATENT DOCUMENTS 5,063,729 A   11/1991   Fox
6,526,357 B1 *  2/2003   Soussan .............. A61M 1/1609
                                                                   702/45
(Continued)

FOREIGN PATENT DOCUMENTS

AU   2001263394   12/2001
SE   0103290      10/2001

OTHER PUBLICATIONS

PCT Search Report and Written Opinion for PCT/EP2019/077662 dated Dec. 9, 2019 (12 pages).
(Continued)

*Primary Examiner* — Benjamin J Klein
*Assistant Examiner* — Erin A Kim
(74) *Attorney, Agent, or Firm* — Mueting Raasch Group (57) ABSTRACT

An extracorporeal blood treatment apparatus, comprises: at least a pressure sensor (24, 25) located in a respective measurement site on an extracorporeal blood circuit (6, 7); an electronic control unit (23) operatively connected at least to the pressure sensor (24, 25). The electronic control unit (23) is configured to perform at least the following procedure: receiving from the pressure sensor (24, 25) a signal correlated to a measured blood pressure (P1measured, P2measured) in the measurement site; correcting the blood measured pressure (P1measured, P2measured) through a mathematical correction model to obtain a blood actual pressure (Pinlet, Poutlet) in a reference site other than the measurement site. Between the reference site and the measurement site, a circuit section and, optionally, at least one additional device (18, 27, 28) is/are positioned. The mathematical correction model is a model of a pressure drop in the circuit section and, optionally, in the additional device (18, 27, 28).

31 Claims, 3 Drawing Sheets (58) Field of Classification Search
CPC ... A61M 2205/3334–3362; A61M 1/14–1698; A61M 1/36–3698
See application file for complete search history.

(56) References Cited

U.S. PATENT DOCUMENTS

| | | |
|---|---|---|
| 7,494,590 B2 | 2/2009 | Felding |
| 2013/0006128 A1 | 1/2013 | Olde |
| 2013/0046226 A1 | 2/2013 | Suffritti |
| 2013/0303961 A1 | 11/2013 | Wolff |
| 2015/0238681 A1* | 8/2015 | Vasta .................. A61M 1/3607 210/97 |
| 2017/0065760 A1 | 3/2017 | Suffritti |
| 2018/0236152 A1* | 8/2018 | Khair .................... B01D 61/32 |

OTHER PUBLICATIONS

Extended European Search Report for Application No. 18199898.0 dated Apr. 8, 2019 (7 pages).

* cited by examiner

EXTRACORPOREAL BLOOD TREATMENT APPARATUS AND METHOD FOR MONITORING PRESSURES IN AN EXTRACORPOREAL BLOOD TREATMENT APPARATUS

This application is a U.S. National Stage Application of International Application No. PCT/EP2019/077662 filed Oct. 11, 2019, which was published in English on Apr. 16, 2020 as International Publication No. WO 2020/074733 A1. International Application No. PCT/EP2019/077662 claims priority to European Application No. 18199898.0 filed Oct. 11, 2018.

FIELD OF THE INVENTION

The present invention relates to an extracorporeal blood treatment apparatus and to method for monitoring pressures in an extracorporeal blood treatment apparatus.

In particular, the present invention relates to the correction of measured pressures in order to monitor actual pressures.

Extracorporeal blood treatment involves removing blood from a patient, treating the blood externally to the patient, and returning the treated blood to the patient. Extracorporeal blood treatment is typically used to extract undesirable matter or molecules from the patient's blood and add desirable matter or molecules to the blood. Extracorporeal blood treatment is used with patients unable to effectively remove matter from their blood, such as when a patient has suffered temporary or permanent kidney failure. These patients and other patients may undergo extracorporeal blood treatment to add or remove matter to their blood, to maintain an acid/base balance or to remove excess body fluids, or to perform extracorporeal gas exchange processes, for example.

Extracorporeal blood treatment is typically accomplished by removing the blood from the patient in e.g. a continuous flow, introducing the blood into a primary chamber, also referred to as blood chamber, of a treatment unit (such as a dialyzer or an hemofilter) where the blood is allowed to flow past a semipermeable membrane. The semipermeable membrane selectively allows matter in the blood to cross the membrane from the primary chamber into a secondary chamber and also selectively allows matter in the secondary chamber to cross the membrane into the blood in the primary chamber, depending on the type of treatment. During extracorporeal blood treatment therapies, pressures are monitored to proper working of the apparatus and/or to allow diagnosing malfunction and failures.

In particular, pressure drops (DP) and transmembrane pressures (TMP), when operating with membrane devices, may be monitored for the purpose of diagnosing blood treatment device plugging (wherein plugging of the device may be caused by accumulation of material in the filter due to excessive filtration on the long run), clotting and/or preventing risk of fiber rupture.

BACKGROUND

These measurements are performed using pressure sensors located in the blood circuit upstream and downstream the blood treatment device, as well as pressure sensor/s placed in the fluid circuit. Sensors in the blood circuit, in the blood withdrawal line and in the blood return line, may be spaced from the blood treatment device. Pipe sections located between pressure sensors and the blood treatment device and additional accessories in the blood circuit (like blood warming devices) and/or development of combined therapies integrating several blood treatment devices in series introduce biases in the pressure measurements performed through said pressure sensors.

Therefore, pressure drops (DP) and transmembrane pressure (TMP) provided by the system through the mentioned pressure sensors are not exact values (overestimated or underestimated). Usually, such values are overestimated due to the presence of neglected pressure drops in series with the blood treatment device and located between upstream and downstream pressure sensors. This overestimated values leads to potential shortened treatments when guided by the occurrence of clotting/clotted alarms or TMP too high alarms.

Document US 2013/0006128 discloses a monitoring device is included in a medical system to implement a method for prediction of a rapid symptomatic drop in a subject's blood pressure, during a medical treatment such as dialysis. A pulse shape parameter with respect to a pulse generator (the heart) of the subject is registered by a pressure sensor arranged in an extracorporeal blood flow circuit coupled to a cardiovascular system of the subject. The pressure sensor is configured to detect pressure variations in blood vessels of the subject. It is investigated, during measurement period, whether or not one or more of the pulse shape parameters fulfil a decision criterion. An output is generated if the decision criterion is found to indicate a predicted rapid symptomatic blood pressure decrease in the subject. The decision criterion may operate on pulse magnitude measures calculated for the received pulse shape parameters, or statistical dispersion measures calculated based on the thus-calculated pulse magnitude measures.

Document US 2017/0065760 shows an apparatus for extracorporeal blood treatment with a treatment unit, a blood removal line and a blood return line, an infusion line of a replacement fluid and a fluid evacuation line connected to the treatment unit. A regulating device of a transmembrane pressure is active on one of the lines and a control unit is configured to command the regulating device by setting a first increase, determine a value of a control parameter corresponding to the first increase, compare the value of the control parameter with a reference value and, if the value of the control parameter is greater than the reference value, command the regulating device by setting a second increase which is greater than the first increase.

SUMMARY OF THE INVENTION

In view of the above, it is an object of embodiments according to the present invention to improve accuracy of blood treatments in extracorporeal blood treatment apparatuses.

It is an object of embodiments according to the present invention to improve controlling the accuracy and reliability of the pressure measurements in extracorporeal blood treatment apparatuses.

In particular, it is an object to provide more accurate pressure drops (DP) and transmembrane pressure (TMP) information.

It is a further object to provide for pressure drops (DP) and transmembrane pressure (TMP) measurements which are independent of the presence of additional devices and/or tube sections.

It is a further object to develop a better malfunction diagnostic (e.g. clotting) based on pressure drops (DP) and transmembrane pressure (TMP) information. This way it is possible to reduce cost by avoiding too early TMP or clotting alarms and achieving a longer use of disposable sets It is a further object to provide said objects without impacting costs of the extracorporeal blood treatment apparatus.

At least one of the above objects is substantially achieved by correcting the pressure measurements using an estimate of pressure drops (due to additional devices, like blood warming devices or gas exchangers and/or tube sections) derived from a mathematical model of said pressure drops in additional devices and/or in circuit sections connecting said devices.

In particular, at least one of the above objects is substantially achieved by an extracorporeal blood treatment apparatus and to a method for monitoring pressures in an extracorporeal blood treatment apparatus according to one or more of the appended claims.

Aspects of the invention are disclosed in the following.

In accordance with a $1^{st}$ independent aspect, an extracorporeal blood treatment apparatus, comprises:
  a blood treatment device;
  an extracorporeal blood circuit coupled to the blood treatment device;
  a blood pump, a pump section of the extracorporeal blood circuit being configured to be coupled to the blood pump;
  optionally, a treatment fluid circuit operatively connected to the extracorporeal blood circuit and/or to the blood treatment device;
  a pressure sensor located in a measurement site on the extracorporeal blood circuit;
  an electronic control unit operatively connected at least to the pressure sensor;
  wherein the electronic control unit is configured to perform at least the following procedure:
  receiving from the pressure sensor a signal correlated to a measured pressure in the measurement site;
  determining a pressure drop between the measurement site and a reference site other than the measurement site, the reference site being a site on the extracorporeal blood circuit, wherein between the reference site and the measurement site, a circuit section and, optionally, at least one additional device is/are positioned.

In a further aspect according to one of the previous aspects, determining a pressure drop is achieved through a mathematical correction model of a pressure drop in the circuit section and, optionally, in the additional device.

In accordance with a $1^{st}$ independent aspect, an extracorporeal blood treatment apparatus, comprises:
  a blood treatment device;
  an extracorporeal blood circuit coupled to the blood treatment device;
  a blood pump, a pump section of the extracorporeal blood circuit being configured to be coupled to the blood pump;
  optionally, a treatment fluid circuit operatively connected to the extracorporeal blood circuit and/or to the blood treatment device;
  a pressure sensor located in a measurement site on the extracorporeal blood circuit;
  an electronic control unit operatively connected at least to the pressure sensor;
  wherein the electronic control unit is configured to perform at least the following procedure:
  receiving from the pressure sensor a signal correlated to a measured pressure in the measurement site;
  correcting the measured pressure through a mathematical correction model to obtain an actual pressure in a reference site other than the measurement site; wherein, between the reference site and the measurement site, a circuit section and, optionally, at least one additional device is/are positioned; wherein the mathematical correction model is a model of a pressure drop in the circuit section and, optionally, in the additional device.

In accordance with a $2^{nd}$ independent aspect, a method for monitoring pressures in an extracorporeal blood treatment apparatus is disclosed,
wherein the extracorporeal blood treatment apparatus comprises: a blood treatment device;
an extracorporeal blood circuit coupled to the blood treatment device;
a blood pump, a pump section of the extracorporeal blood circuit being configured to be coupled to the blood pump;
optionally, a treatment fluid circuit operatively connected to the extracorporeal blood circuit and/or to the blood treatment device;
at least a pressure sensor located in a respective measurement site on the extracorporeal blood circuit;
wherein the method comprises:
  receiving from the pressure sensor a signal correlated to a measured blood pressure in the measurement site;
  correcting the blood measured pressure through a mathematical correction model to obtain a blood actual pressure in a reference site other than the measurement site; wherein, between the reference site and the measurement site, a circuit section and, optionally, at least one additional device is/are positioned; wherein the mathematical correction model is a model of a pressure drop in the circuit section and, optionally, in the additional device.

In a further aspect according to one of the previous aspects, the reference site is a reference site on the extracorporeal blood circuit.

In a further aspect according to one of the previous aspects, the reference site is closer to the blood treatment device than the measurement site.

In a further aspect according to one of the previous aspects, the measuring site is in a location between the blood pump and the blood treatment device.

In a further aspect according to one of the previous aspects, the electronic control unit is configured to calculate a transmembrane pressure of the blood treatment device as a function of the blood actual pressure in the reference site.

In a further aspect according to one of the previous aspects, the electronic control unit is configured to calculate a transmembrane pressure of the blood treatment device as a function of the measured blood pressure in the measurement site and a determined pressure drop between the measurement site and the reference site, in particular a mean value of the measured blood pressure in the measurement site and the determined pressure drop.

In a further aspect according to one of the previous aspects, the apparatus comprises an auxiliary pressure sensor located on an auxiliary measuring site either in the extracorporeal blood treatment or in the treatment fluid circuit, wherein the electronic control unit is configured to:
  receive from the auxiliary pressure sensor a signal correlated to a measured auxiliary pressure in the auxiliary measuring site;
  optionally correct the auxiliary measured pressure through an auxiliary mathematical correction model to obtain an actual auxiliary pressure in an auxiliary reference site other than the auxiliary measurement site; wherein, between the auxiliary reference site and the auxiliary measurement site, an auxiliary circuit section and, optionally, at least one additional device is/are positioned; wherein the auxiliary mathematical correction model is a model of an auxiliary pressure drop in the auxiliary circuit section and, optionally, in the additional device;

optionally determine an auxiliary pressure drop between the auxiliary measurement site and the auxiliary reference site;

calculate a trans-membrane pressure of the blood treatment device as a function of:
    either the blood actual pressure in the reference site; or the measured blood pressure in the measurement site and the determined pressure drop between the measurement site and the reference site; and
    either an actual pressure in an auxiliary reference site; or the measured pressure in the auxiliary measurement site and a determined pressure drop between the auxiliary measurement site and the auxiliary reference site; or the measured pressure in the auxiliary measurement site.

In a further aspect according to the previous aspect, the extracorporeal blood circuit comprises a blood withdrawal line and a blood return line and the pressure sensor is located on the blood withdrawal line or on the blood return line and the auxiliary pressure sensor is located on the other of the blood withdrawal line and the blood return line.

In a further aspect according to the previous aspect, the extracorporeal blood circuit comprises a blood withdrawal line and a blood return line and the pressure sensor is located on the blood withdrawal line or on the blood return line and the auxiliary pressure sensor is located on the treatment fluid circuit, particularly on an effluent line of the treatment fluid circuit.

In a further aspect according to one of the previous aspects, the electronic control unit is configured to process the signal correlated to the measured pressure of the blood in the measurement site to obtain a mean value of the blood pressure in the measurement site.

In a further aspect according to one of the previous aspects, the electronic control unit is connected to the pressure sensor located in the measurement site, and to the blood pump, and is configured:
    to move the blood pump such as to generate a variable blood flow comprising a constant flow component of a desired blood flow value and a variable flow component having a substantially nil mean value, the variable blood flow generating at least in the measurement site a pressure progression that is variable in time (P(t)) comprising a pressure component ($\Delta P(t)$) oscillating about a mean value ($P_{avg}$);
    to receive from the pressure sensor a plurality of pressure values ($P_j$) for a time period (T) comprising at least one, and in particular a plurality, of pressure oscillations about the mean value ($P_{avg}$) the pressure values ($P_j$) being measured at successive time instants ($t_j$).

For example, time periods of 3 to 7 oscillations are used for each pressure mean value calculation. Notably also time period shorter than one pressure oscillation caused by the blood pump may be used if sufficient to determine a mean pressure value.

In a further aspect according to one of the previous aspects, the signal correlated to a measured pressure in the measurement site comprises (namely, is) a pressure progression that is variable in time (P(t)) comprising a pressure component ($\Delta P(t)$) oscillating about a mean value ($P_{avg}$).

In a further aspect according to one of the previous three aspects, the electronic control unit is configured to correct the mean value ($P_{avg}$) of the measured pressure through the mathematical correction model.

In a further aspect according to one of the previous four aspects, the electronic control unit is configured to determine the pressure drop of the mean value ($P_{avg}$) of the measured pressure between the measurement site and the reference site.

In a $3^{rd}$ aspect according to one of the previous aspects, the circuit section is a tube section, wherein optionally a length of the tube section is between 200 mm to 1000 mm, wherein optionally the circuit section comprises one or more connectors, like male/female Luer connectors.

In a $4^{th}$ aspect according to one of the previous aspects, said at least one additional device is a blood warming device or a gas exchanger or a hemoperfusion device or another additional blood treatment device; wherein optionally the blood warming device comprises or it is configured to be coupled to a blood warming bag or cassette delimiting a blood path.

In a $5^{th}$ aspect according to one of the previous aspects, the apparatus comprises or is configured to be coupled to the additional device.

In a $6^{th}$ aspect according to any of the previous aspects, the extracorporeal blood circuit comprises a blood withdrawal line and a blood return line and the pressure sensor is located on the blood withdrawal line and/or on the blood return line.

In a $7^{th}$ aspect according to the previous aspect, the blood treatment device presents a blood inlet port connected to the blood withdrawal line and a blood outlet port connected to the blood return line and optionally the pressure sensor is spaced from the blood inlet port and/or from the blood outlet port, optionally with a distance between 200 mm to 1000 mm.

In an $8^{th}$ aspect according the previous aspect, the blood treatment device comprises a blood chamber and a fluid chamber separated from one another by a semipermeable membrane, wherein the blood chamber has the blood inlet port and the blood outlet port.

In a $9^{th}$ aspect according any of the previous aspects 6 or 7 or 8, the pressure sensor comprises a first pressure sensor located on the blood withdrawal line upstream the blood treatment device.

In a $10^{th}$ aspect according to the previous aspect, the pressure sensor comprises a second pressure sensor located on the blood return line downstream the blood treatment device.

In an $11^{th}$ aspect according to the previous aspect 9 or 10, the method comprises or the electronic control unit is configured to perform at least the following procedure:
    receiving from the first pressure sensor a signal correlated to a first measured blood pressure upstream the blood treatment device;
    correcting the first measured blood pressure through a first mathematical correction model to obtain a first actual blood pressure Pinlet at the blood inlet port of the blood treatment device.

In an 11A aspect according to the previous aspect 9 or 10, the method comprises or the electronic control unit is configured to perform at least the following procedure:
    receiving from the first pressure sensor a signal correlated to a first measured blood pressure upstream the blood treatment device;

determining a first pressure drop between the measurement site of the first pressure sensor and the reference site other than the measurement site, in particular the reference site being closer to the blood treatment unit than the measurement site, a first actual blood pressure Pinlet at the blood inlet port of the blood treatment device being function of the first measured blood pressure and the first pressure drop and being obtainable through a first mathematical correction model.

In a 12$^{th}$ aspect according to any of the previous aspects 10 or 11 when according to aspect 10, the method comprises or the electronic control unit is configured to perform at least the following procedure:

receiving from the second pressure sensor a signal correlated to a second measured blood pressure downstream the blood treatment device;

correcting the second blood measured pressure through a second mathematical correction model to obtain a second blood actual pressure Poutlet at the blood outlet port of the blood treatment device.

In a 12A aspect according to any of the previous aspects 10 or 11 when according to aspect 10, the method comprises or the electronic control unit is configured to perform at least the following procedure:

receiving from the second pressure sensor a signal correlated to a second measured blood pressure downstream the blood treatment device;

determining a second pressure drop between the measurement site of the second pressure sensor and the reference site other than the measurement site, in particular the reference site being closer to the blood treatment unit than the measurement site, a second actual blood pressure Poutlet at the blood outlet port of the blood treatment device being function of the second measured blood pressure and the second pressure drop and being obtainable through a second mathematical correction model.

In a 13$^{th}$ aspect according to the previous aspect 12 when according to aspect 11, the method comprises or the electronic control unit is configured to perform at least the following procedure: calculating an actual pressure drop of the blood treatment device as a difference between the first actual blood pressure and the second blood actual pressure; and optionally triggering an alarm if the actual pressure drop is outside a pressure drop safe range.

In a 14$^{th}$ aspect according to aspect 8 or to any of aspects 9 to 13 when according to aspect 8, the fluid chamber has at least a fluid outlet port and the treatment fluid circuit comprises an effluent line connected with the fluid outlet port of the fluid chamber such as to receive a filtered waste fluid through the semipermeable membrane.

In a 15$^{th}$ aspect according to aspect 8 or to any of aspects 9 to 14 when according to aspect 8, the fluid chamber has at least a fluid inlet port and the treatment fluid circuit comprises a dialysis line connected with the fluid inlet port of the fluid chamber.

In a 16$^{th}$ aspect according to the previous aspect 14 or to aspect 15 when according to aspect 14, the apparatus comprises at least an effluent pressure sensor placed on the effluent line and the method comprises or the electronic control unit is configured to perform at least the following procedure: receiving from the effluent pressure sensor a signal correlated to a filtered waste fluid pressure Peffluent.

In a 17$^{th}$ aspect according to the previous aspect 16, the method comprises or the electronic control unit is configured to perform at least the following procedure: calculating an actual access trans-membrane pressure of the blood treatment device as a difference between the first actual blood pressure and the filtered waste fluid pressure; and optionally triggering an alarm if the actual trans-membrane pressure is outside an access transmembrane pressure safe range.

In an 18$^{th}$ aspect according to aspect 16 when according to aspect 15, the electronic control unit is configured to perform at least the following procedure: calculating an actual trans-membrane pressure of the blood treatment device through the formula ((Pinlet+Poutlet)/2)−Peffluent; and optionally triggering an alarm if the actual trans-membrane pressure is outside an actual trans-membrane pressure safe range.

In a 19$^{th}$ aspect according to any of the previous aspects, a deaeration chamber is placed on the blood return line and/or in the blood withdrawal line.

In a 20$^{th}$ aspect according to the previous aspect, the pressure sensor, optionally the second pressure sensor or the first pressure sensor, is positioned in the deaeration chamber.

In a 21$^{st}$ aspect according to the previous aspect, the reference site is at the blood outlet port of the blood treatment device.

In a 22$^{nd}$ aspect according to aspect 20 or 21, said at least one additional device is placed on the blood return line between the blood treatment device and the deaeration chamber. Optionally, said at least one additional device is placed on the blood withdrawal line between and the deaeration chamber and the blood treatment device.

In a 23$^{rd}$ aspect according to any of the previous aspects, the mathematical correction model is built from physical equations.

In a 24$^{th}$ aspect according to any of the previous aspects, the mathematical correction model is a function of geometry of the circuit section, optionally of dimensions and loss coefficient.

In a 25$^{th}$ aspect according to any of the previous aspects, the mathematical correction model is a function of geometry of the additional device, optionally of dimensions and loss coefficient.

In a 26$^{th}$ aspect according to any of the previous aspects, the mathematical correction model is a function of blood kinematic or dynamic viscosity related to the circuit section or the additional device.

In a 27$^{th}$ aspect according to any of the previous aspects, the mathematical correction model is a function of blood flow rate in the circuit section or in the additional device.

In a 28$^{th}$ aspect according to any of the previous aspects, the mathematical correction model is a function of blood haematocrit.

In a 29$^{th}$ aspect according to any of the previous aspects, the mathematical correction model is a function of blood temperature, optionally measured or estimated.

In a 30$^{th}$ aspect according to any of previous aspects, the mathematical correction model is a function of blood protein concentration, optionally albumin or total proteins.

In a 31$^{st}$ aspect according to the previous aspect when according to aspect 26, kinematic or dynamic blood viscosity is estimated and optimized through blood temperature and/or blood protein concentration.

In a 32$^{nd}$ aspect according to any of previous aspects, the mathematical correction model is a function of blood density.

In a 33$^{rd}$ aspect according to the previous aspect, the blood density is estimated as a function of blood haematocrit and water density and optionally blood protein concentration.

In a 34$^{th}$ aspect according to any of the previous aspects 1 to 22, the mathematical correction model is an empirical model of a measurement error derived from a plurality of experimental data sets, the measurement error being a difference between the blood measured pressure in the measurement site and the blood actual pressure in the reference site.

In a 35$^{th}$ aspect according to the previous aspect, the mathematical correction model is derived from a regression analysis of the measurement error collected through said plurality of experimental data sets versus a one or more parameter collected through said plurality of experimental data sets.

In a 36$^{th}$ aspect according to the previous aspect, said parameters comprise the blood measured pressure and at least one further working parameter of the extracorporeal blood treatment apparatus and/or the additional device.

In a 37$^{th}$ aspect according to the previous aspect, the at least one further working parameter comprises the blood flow rate.

In a 38$^{th}$ aspect according to any of the previous aspects, the blood treatment device is a hemofilter or a hemodiafilter or a plasmafilter or a dialysis filter or an absorber.

DESCRIPTION OF DRAWINGS

The following drawings relating to aspects of the invention are provided by way of non-limiting example.

DETAILED DESCRIPTION

Figure 1:
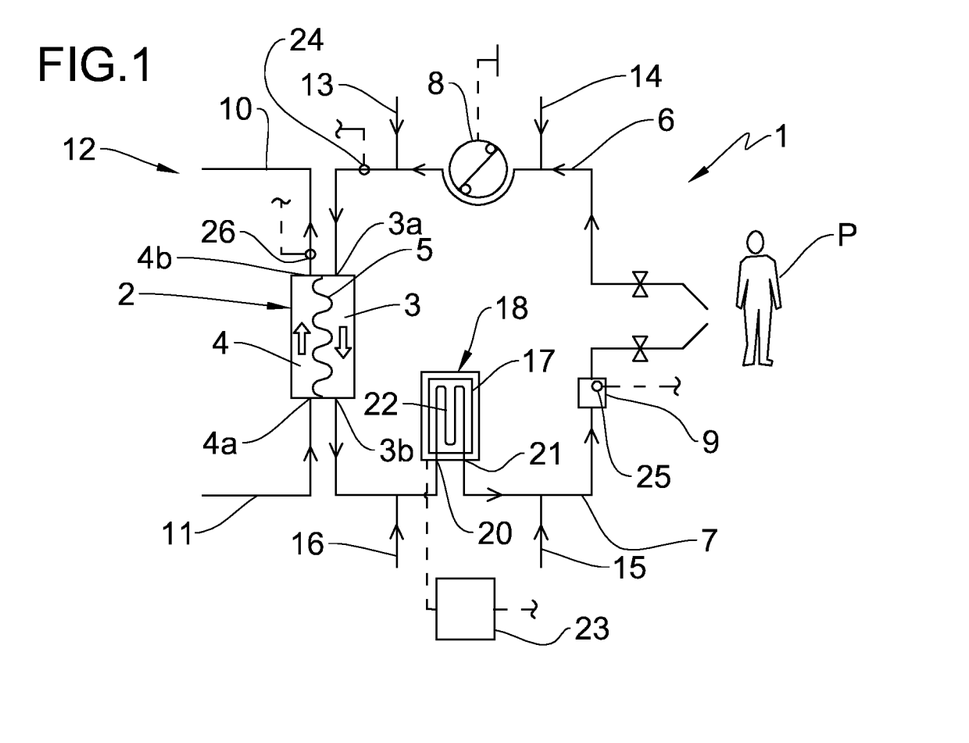
FIG. 1 shows an extracorporeal blood treatment apparatus according to the present invention.

With reference to the appended drawings, FIG. 1 shows a schematic representation of an extracorporeal blood treatment apparatus 1. The apparatus 1 comprises one blood treatment device 2, for example a hemofilter, a hemodiafilter, a plasmafilter, a dialysis filter, an absorber or other unit suitable for processing the blood taken from a patient P.

The blood treatment device 2 has a first compartment or blood chamber 3 and a second compartment or fluid chamber 4 separated from one another by a semipermeable membrane 5. A blood withdrawal line 6 is connected to an inlet port 3a of the blood chamber 3 and is configured, in an operative condition of connection to the patient P, to remove blood from a vascular access device inserted, for example in a fistula on the patient P. A blood return line 7 connected to an outlet port 3b of the blood chamber 3 is configured to receive treated blood from the treatment unit 2 and to return the treated blood, e.g. to a further vascular access also connected to the fistula of the patient P. Note that various configurations for the vascular access device may be envisaged: for example, typical access devices include a needle or catheter inserted into a vascular access which may be a fistula, a graft or a central (e.g. jugular vein) or peripheral vein (femoral vein) and so on.

The blood withdrawal line 6 and the blood return line 7 are part of an extracorporeal blood circuit of the apparatus 1. The extracorporeal blood circuit 6, 7 and the treatment unit 2 are usually disposable parts which are loaded onto a frame of a blood treatment machine, not shown.

As shown in FIG. 1, the apparatus 1 comprises at least a first actuator, in the present example a blood pump 8, which is part of said machine and operates at the blood withdrawal line 6, to cause movement of the blood removed from the patient P from a first end of the withdrawal line 6 connected to the patient P to the blood chamber 3. The blood pump 8 is, for example, a peristaltic pump, as shown in FIG. 1, which acts on a respective pump section of the withdrawal line 6.

It should be noted that for the purposes of the present description and the appended claims, the terms "upstream" and "downstream" may be used with reference to the relative positions taken by components belonging to or operating on the extracorporeal blood circuit. These terms are to be understood with reference to a blood flow direction from the first end of the blood withdrawal line 6 connected to the patient P towards the blood chamber 3 and then from the blood chamber 3 towards a second end of the blood return line 7 connected to the vascular access of the patient P.

The apparatus 1 may further comprise an air trapping device operating on the blood return line 7. The air trapping device may be a venous deaeration chamber 9. The deaeration chamber 9 is placed online in the blood return line 7.

A first section of the blood return line 7 puts in fluid communication the outlet port 3b of the blood chamber 3 with the deaeration chamber 9 and a second section of the blood return line 7 puts in fluid communication the deaeration chamber 9 with the patient P. The blood coming from the blood chamber 3 of the treatment device 2 enters and exits the deaeration chamber 9 before reaching the patient P.

An air trapping device may also be present on the blood withdrawal line. Said air trapping device ensures that blood is essentially free of air/air bubbles before entering the blood treatment device 2.

The apparatus 1 of FIG. 1 further comprises one effluent line 10 connected with a fluid outlet port 4b of the fluid chamber 4 such as to receive the filtered waste fluid through the semipermeable membrane 5. The effluent line 10 receives such filtered waste fluid coming from the fluid chamber 4 of the treatment device 2, for example, comprising used dialysis liquid and/or liquid ultra-filtered through the membrane 5. The effluent line 10 leads to a receiving element, not shown, for example having a collection bag or a drainage pipe for the waste fluid. One or more dialysate pumps, not shown, may operate on the effluent line 10.

In the example of FIG. 1, a dialysis line 11 is also present for supplying a fresh treatment fluid into a fluid inlet port 4a of the fluid chamber 4. The presence of this dialysis line 11 is not strictly necessary since, in the absence of the dialysis line 11, the apparatus 1 is still able to perform treatments such as ultrafiltration, hemofiltration or plasma-filtration. In case the dialysis line 11 is present, a fluid flow intercept device may be used, not shown, to selectively allow or inhibit fluid passage through the dialysis line 11, depending on whether or not a purification by diffusive effect is to be performed inside the treatment device 2.

Figure 2:
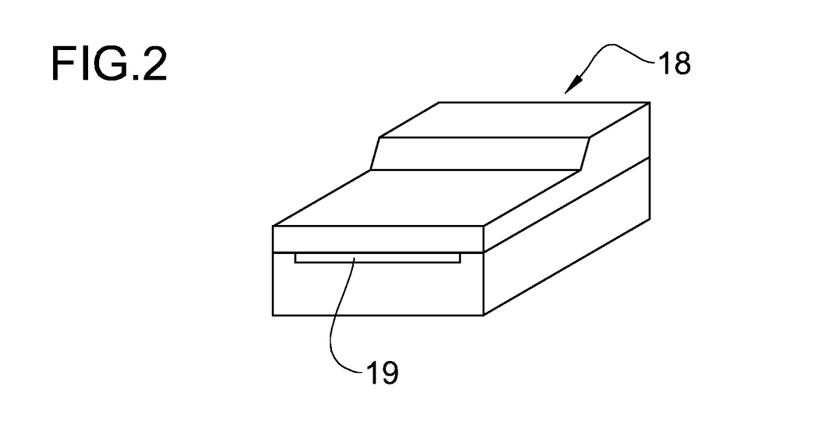
FIG. 2 shows blood warming device of the extracorporeal blood treatment apparatus of FIG. 1.
Figure 3:
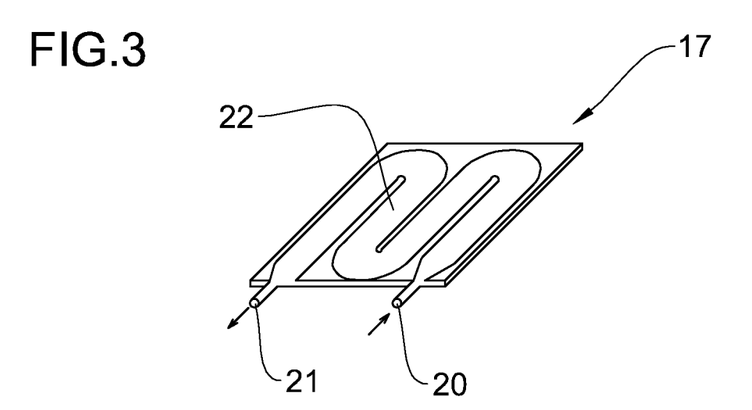
FIG. 3 shows a blood warming bag insertable into the blood warming device of FIG. 2.

The dialysis line 11, if present, is typically equipped with a dialysis pump and is able to receive a fresh fluid from a module, not shown, for example a bag or on-line preparation section of dialysis fluid, and to send such a fluid to the fluid inlet port 4a of the fluid chamber 4. The effluent line 10, the dialysis line 11 and the fluid chamber 4 are part of a treatment fluid circuit 12. The apparatus 1 as shown in FIG. 1 further comprises an infusion circuit comprising one or more infusion lines of a replacement fluid. According to the embodiment of FIG. 1, a pre-infusion line 13 is connected to the blood withdrawal line 6 between the blood pump 8 and the inlet port 3a of the blood chamber 3. A pre pump infusion line 14 is connected to the blood withdrawal line 6 upstream of the blood pump 8, between said blood pump 8 and the vascular access device inserted in the fistula on the patient P. A post-infusion line 15, 16 is connected to the blood return line 7 for performing HF or HDF treatments. Generally one or two post-infusion lines are used connected upstream of or to the air trapping device 9. FIG. 1 shows that the post-infusion line comprises a first and a second branch 15, 16. Each of the pre- and/or post-infusion line 13, 14, 15, 16 is provided with a respective pump, not shown. The pre- and/or post-infusion lines 13, 14, 15, 16 may be supplied by fluid coming from bags or directly by infusion fluid prepared on-line. Each of the pre- and/or post-infusion lines 13, 14, 15, 16 are part of the treatment fluid circuit 12. The specific configuration of the pre- and post-infusion circuits may of course differ from those shown in FIG. 1. The blood return line 7 presents a heating zone, for example interposed between the first and second branches 15, 16 of the post-infusion line. In said heating zone blood is warmed before flowing into the blood circulation system of the patient P. In the embodiment shown in the attached figures, the heated portion is part of a disposable blood warming bag 17 which is inserted into a blood warming device 18 (FIGS. 2 and 3). The blood warming device 18 is connected to or is part of the extracorporeal blood treatment apparatus 1.

The blood warming bag 17 is a substantially flat and soft bag insertable through a slot 19 in a heating seat provided in the blood warming device 18 (FIGS. 2 and 3).

The blood warming bag 17 presents an inlet 20 and an outlet 21 connected to the extracorporeal blood circuit. For instance, the blood warming bag 17 comprises two sheets of plastic (e.g. polyurethane or polyvinylchloride) superposed and welded to form the bag and to form, inside the bag, a blood warming path 22 delimited by said two sheets and by lines of welding.

The apparatus 1 further comprises an electronic control unit 23. The electronic control unit 23 may comprise a digital processor (CPU) and memory (or memories), an analog circuit, or a combination thereof, and input/output interfaces. Said control unit 23 is configured to control the apparatus 1 during patient blood treatment through a software stored in the control unit 23. In the embodiment of FIG. 1, the electronic control unit 23 is connected at least to the blood pump 8 and to the power control unit, not shown, of the blood warming device 18.

A first pressure sensor 24 is located on the blood withdrawal line 6 upstream the blood treatment device 2 and downstream the blood pump 8. The first pressure sensor 24 may be close to the blood inlet port 3a (the length of tube between the first pressure sensor 24 and the blood inlet port may be only some centimeters) or may be spaced from the blood inlet port (the tube section between the first pressure sensor 24 and the blood inlet port may be decimeters, e.g. 200 mm).

A second pressure sensor 25 is located on the blood return line 6 downstream the blood treatment device 2. In the embodiment of FIG. 1, the second blood pressure sensor 25 is placed inside the deaereation chamber 9. The deaereation chamber 9 may comprise a casing delimiting a volume for blood and the second pressure sensor 25 is placed on a upper part of the deaereation chamber 9 above blood, to sense pressure of a gas (e.g. air) filling the space above a free blood surface. The second pressure sensor 25 is spaced from the blood outlet port 3b (e.g. of 1000 mm tube section) and furthermore, the disposable blood warming bag 17 with the blood warming path 22 is placed between the blood outlet port 3b and said second pressure sensor 25.

If an air trapping device/deaereation chamber is placed also on the blood withdrawal line 6, the first blood pressure sensor 24 may be placed inside said deaereation chamber.

The tube sections and possible connectors (e.g. male/female Luer connectors) generate pressure drop in blood flowing through. The blood warming device 18 with the blood warming bag 17 is an additional device which the blood flows through and which generates an additional pressure drop in blood.

An effluent pressure sensor 26 is also placed on the effluent line 10 to sense pressure of waste fluid. A dialysis pressure sensor 26a might be on the dialysis line 11, in addition to or in lieu of the effluent pressure sensor 26.

Figure 4:
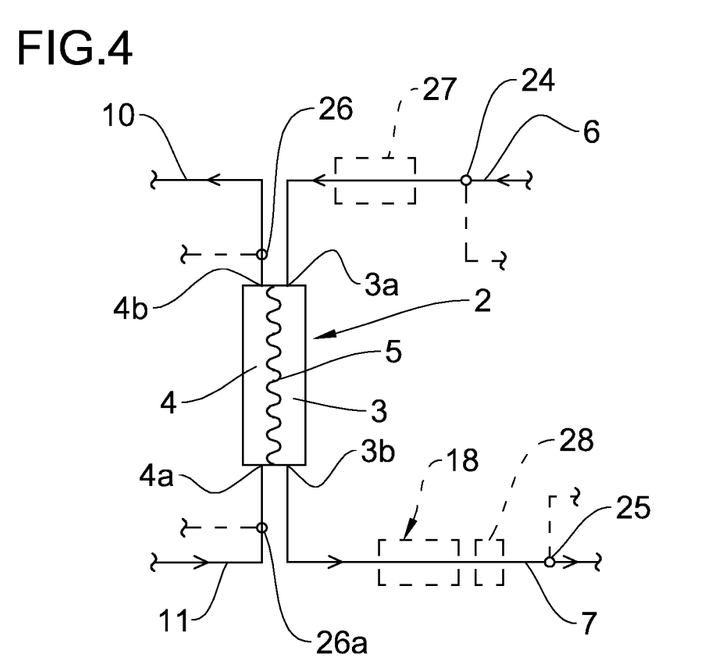
FIG. 4 shows a schematic representation of a portion of the an extracorporeal blood treatment apparatus according to the present invention.
Figure 5:
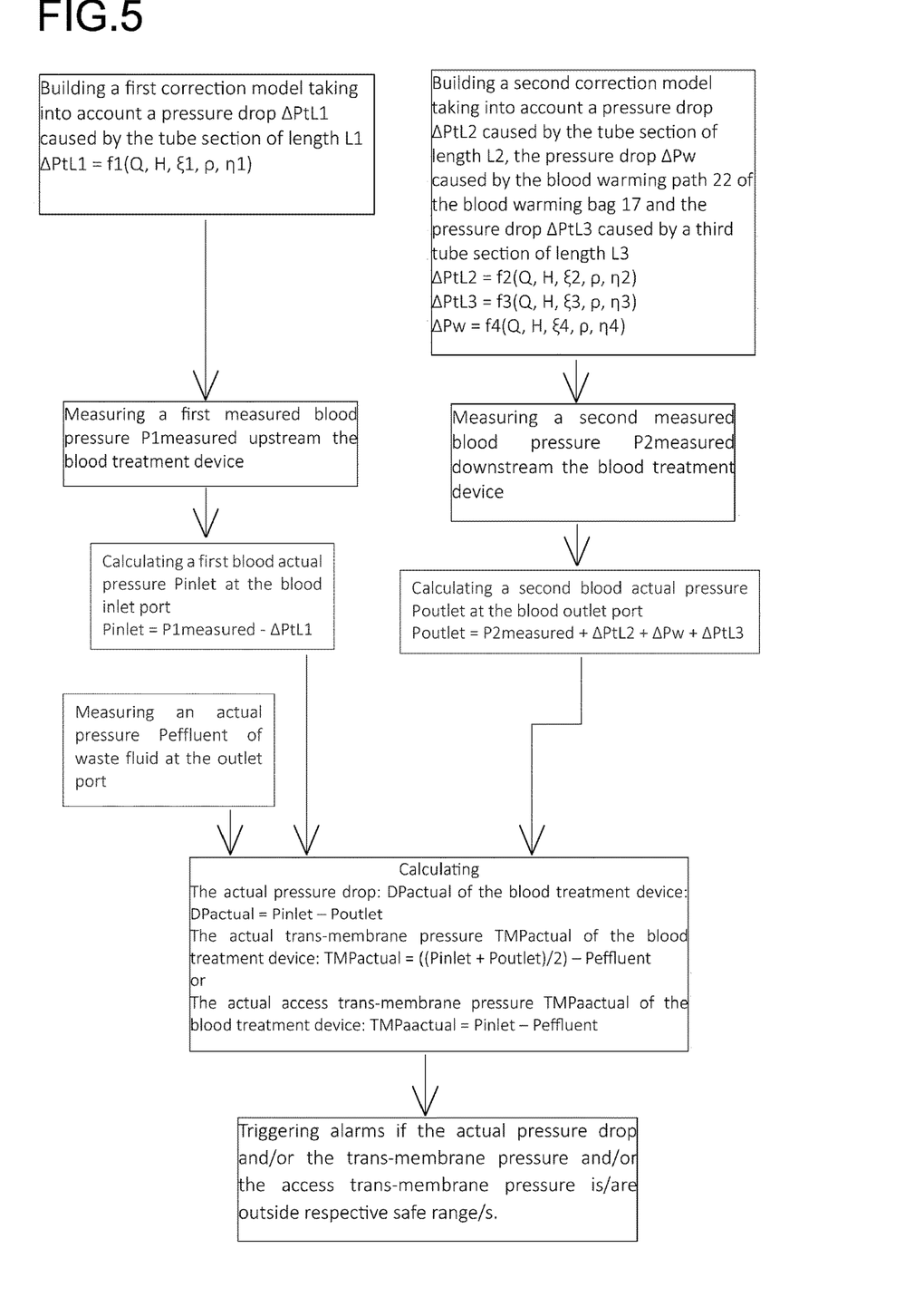
FIG. 5 is a flowchart showing steps of a method according to the invention.

In other embodiments, like the one schematically represented in FIG. 4, a further additional device 27 generating a pressure drop may be placed on the blood withdrawal line 6, between the first pressure sensor 24 and the blood inlet port 3a. Another additional device 28 generating a respective pressure drop may also be placed on the blood return line 7, between the blood warming device 18 and the second pressure sensor 25.

The first pressure sensor 24, the second pressure sensor 25 and the effluent pressure sensor 26 are operatively connected to the electronic control unit 23 to send to said electronic control unit 23 signals correlated to the sensed pressures.

At least during the treatment, the control unit moves the blood pump to generate a variable flow of blood comprising a constant flow component equal to a desired blood flow value and a variable flow component at substantially zero average value. This is due in particular to the fact that the blood pump is peristaltic in nature and therefore produces a non-constant flow of blood in the circuit, as it is related to the successive squeezing actions of the pump section by the roller/rollers associated to the pump rotor.

In other words, the hydraulic head of the treated fluid is given by a constriction which runs along the tube. In an example, the pump is constituted by a rotor to which two (or more rollers) are applied, which rotate to "squeeze" the tube and cause the advancement of the fluid. Alternatively linear peristaltic pumps may be used (for example, "finger" pumps) or also other actuators capable of generating a pulsating movement in the blood, i.e. a non-constant flow, but oscillating about an average flow value.

Alternatively the control unit might control the pump to generate the pulsating movement in the blood in order to use other kinds of pumps which do not have the pressure variations inherently generated. Consequently the variable blood flow generates in the blood circuit a pressure trend that is time-variable P(t) comprising a pressure component $\Delta P(t)$ oscillating about an average value $P_{avg}$.

The control unit is programmed to receive, from the pressure sensors located in their respective positions, a plurality of pressure values $P_j$ for a period of time T (typically coinciding with the treatment period). A minimum time period $T_{min}$ for which the detected pressure data $P_j$ are used, comprises at least one and in particular a plurality of oscillations of the pressure about the average value $P_{avg}$; in particular, time periods of 3-7 oscillations are used for each calculation of a mean pressure value used for the TMP calculation as below described.

Obviously the pressure values $P_j$ are measured in discrete and successive time instants $t_j$. The sampling timing may be constant, depending on the type of pressure sensor used and possibly other parameters of apparatus operation.

According to the apparatus and method of the invention, the electronic control unit 23 is configured to receive from the first pressure sensor 24, from the second pressure sensor 25 and from the effluent pressure sensor 26 respective signals correlated to the measured pressures in the respective sites, to correct at least some of the measured pressures and to compute pressure differences useful to monitor the blood treatment process performed by the apparatus 1.

In order to correct the measured blood pressures, one or more correction mathematical models or algorithms is/are previously developed and stored in a memory of the electronic control unit 23 or connected to the electronic control unit 23. The mathematical correction model/s is/are model/s of pressure drop/s in the circuit section/s and in the additional device/s. Through the mathematical correction model/s, actual pressures in reference sites other than the measurement sites is/are obtained.

Referring to the embodiment of FIG. 1, the electronic control unit 23 receives from the first pressure sensor 24 a signal correlated to a first measured blood pressure P1measured upstream the blood treatment device 2 and corrects the first measured blood pressure P1measured through a first mathematical correction model to obtain a first actual blood pressure Pinlet at the blood inlet port 3a of the blood treatment device 2.

The first correction model takes into account a pressure drop $\Delta PtL1$ caused by the tube section of length L1 (e.g. 200 mm) between the first pressure sensor 24 and the blood inlet port 3a.

$$Pinlet = P1measured - \Delta PtL1 \qquad \text{i)}$$

The first mathematical correction model of the pressure drop $\Delta PtL1$ caused by the tube section may be built from the following physical equation:

$$\Delta PtL1 = f1(Qb, H, \tau 1, \rho, \eta 1) \qquad \text{ii)}$$

where
Qb blood flow rate
H blood hematocrit
$\rho$ blood density
$\xi 1$ loss coefficient of tube
$\eta 1$ kinematic viscosity in tube Equation ii) takes also into account the geometry of the tube and connector/s, e.g. male/female Luer connectors. The density of blood may be estimated as a function blood hematocrit and water density $\rho w$.

The electronic control unit 23 receives from the second pressure sensor 25 a signal correlated to a second measured blood pressure P2measured downstream the blood treatment device 2 and corrects the second blood measured pressure P2measured through a second mathematical correction model to obtain a second blood actual pressure Poutlet at the blood outlet port 3b of the blood treatment device 2.

The second correction model takes into account a pressure drop $\Delta PtL2$ caused by the tube section of length L2 (e.g. 250 mm) between the blood outlet port 3b and the blood warming device 18, the pressure drop $\Delta Pw$ caused by the blood warming path 22 of the blood warming bag 17 and the pressure drop $\Delta PtL3$ caused by a tube section of length L3 (e.g. 250 mm) between the blood warming device 18 and the second pressure sensor 25.

$$Poutlet = P2measured + \Delta PtL2 + \Delta Pw + \Delta PtL3 \qquad \text{iii)}$$

Physical equations for $\Delta PtL2$ and $\Delta PtL3$ are similar to ii).

$$\Delta PtL2 = f2(Q, H, \xi 2, \rho, \eta 2) \qquad \text{iv)}$$

$\xi 2$ loss coefficient of tube
$\eta 2$ kinematic viscosity in tube $$\Delta PtL3 = f3(Q, H, \xi 3, \rho, \eta 3) \qquad \text{v)}$$

$\xi 3$ loss coefficient of tube
$\eta 3$ kinematic viscosity in tube

Physical equation caused by blood warming bag is:

$$\Delta Pw = f4(Q, H, \xi 4, \rho, \eta 4) \qquad \text{vi)}$$

where
Qb blood flow rate
H blood hematocrit
$\rho$ blood density
$\xi 4$ loss coefficient of bag
$\eta 4$ kinematic viscosity in bag Equation vi) takes also into account the geometry of bag and connector/s. The density of blood may be estimated as a function blood hematocrit and water density $\rho w$.

The kinematic viscosity description of blood includes the variables shear rate, hematocrit and protein content of blood. For the tube section and bag respectively this gives:

$$\eta 1 = f5(\mu pl, k1, \rho, H) \qquad \text{vii)}$$

$$n2 = f6(\mu pl, k2, \rho, H) \qquad \text{viii)}$$

where
$\mu pl$ is the dynamic plasma viscosity which may be defined as function of protein content Cp (e.g. albumin or total proteins).
Cp may also be estimated from hematocrit H.
k1, k2 are shear dependent intrinsic viscosity in tube and bag which may be defined as function of hematocrit H.
To optimize kinematic viscosity description, blood temperature may also be included.

Therefore, in order to build physical equations of the correction models (estimating blood pressure drops in different devices/circuit sections) data needed may be:
H hematocrit value
Qb blood flow rate
$\rho w$ water density
Cp protein content
Geometry of devices/circuit sections (lengths, diameters, loss coefficients, etc.)

Blood flow Qb, hematocrit H, temperature and total protein concentration Cp may change in the various sections of the blood circuit according to infusions in the pre- and/or post-infusion lines 13, 14, 15, 16 and/or ultrafiltration in the blood treatment device 2.

Alternatively, the correction models may be built using a more empirical approach. The mathematical correction model is an empirical model of a measurement error E derived from a plurality of experimental data sets, e.g. gathered during development testing. The measurement error E may be a difference between the blood measured pressure in the measurement site and the blood actual pressure in the reference site.

The empirical mathematical correction model is built by carrying out a plurality of test treatments. An experimental data set is collected for each test treatment. Each experimental data set comprises a one or more measured parameters.

The mathematical correction model may be derived from a regression analysis of the measurement error E collected through said plurality of experimental data sets versus the mentioned parameter/s collected through said plurality of experimental data sets. The model will be as reliable as the experimental data set collection is large. Regression model may be streamlined as linear versus blood flow rate Qb.

The electronic control unit 23 further receives from the effluent pressure sensor 26 a signal correlated to the measured pressure P3m of waste fluid. The effluent pressure sensor 26 is close to the fluid outlet port 4b and the measured pressure of waste fluid P3m may be considered as an actual pressure Peffluent of waste fluid at the outlet port 4b.

The electronic control unit 23 is programmed to calculate an actual pressure drop DPactual of the blood treatment device 2 as a difference between the first actual blood pressure Pinlet and the second blood actual pressure Poutlet.

$$DPactual = Pinlet - Poutlet \qquad \text{viii)}$$

If no correction of measured pressures were performed, the measured pressure drop DPmeasured of the blood treatment device 2 would be:

$$Dpmeasured = Dpactual + (\Delta PtL1 + \Delta PtL2 + \Delta Pw + \Delta PtL3) \qquad \text{ix)}$$

The measured pressure drop Dpmeasured of the blood treatment device 2 would be overestimated with respect to the actual pressure drop Dpactual of the blood treatment device 2. A difference between the measured pressure drop Dpmeasured and the actual pressure drop Dpactual may be e.g. between 50 mmHg and 200 mmHg.

The electronic control unit 23 is programmed to calculate an actual trans-membrane pressure TMPactual of the blood treatment device 2 through the formula:

$$TMPactual = ((Pinlet + Poutlet)/2) - Peffluent \qquad \text{x)}$$

If no correction of measured pressures were performed, the measured trans-membrane pressure TMPmeasured would be:

$$TMPmeasured = TMPactual + ((\Delta PtL1 - (\Delta PtL2 + \Delta Pw + \Delta PtL3))/2) \qquad \text{xi)}$$

Depending on values of $\Delta PtL1$ and $(\Delta PtL2 + \Delta Pw + \Delta PtL3)$, the measured trans-membrane pressure TMPmeasured would be overestimated or underestimated with respect to the actual transmembrane pressure TMPactual. A difference between the measured trans-membrane pressure TMPmeasured and the actual trans-membrane pressure TMPactual may be e.g. between +/−10 mmHg and +/−50 mmHg.

If plasmapheresis is performed, the electronic control unit 23 is programmed to calculate an actual access transmembrane pressure TMPaactual of the blood treatment device 2 (plasmafilter).

$$TMPaactual = Pinlet - Peffluent \qquad \text{xii)}$$

If no correction of measured pressures were performed, the measured access trans-membrane pressure TMPameasured would be:

$$TMPameasured = TMPaactual + \Delta PtL1 \qquad \text{xiii)}$$

The measured access trans-membrane pressure TMPameasured would be overestimated with respect to the actual access trans-membrane pressure TMPaactual. A difference between the measured access trans-membrane pressure TMPameasured and the actual access transmembrane pressure TMPaactual may be e.g. between 20 mmHg and 50 mmHg.

The actual pressure drop (DPactual) and actual transmembrane pressures (TMPactual and TMPaactual) may be monitored for the purpose of diagnosing blood treatment device plugging (excessive filtration), clotting and/or preventing risk of fiber.

By way of example, the electronic control unit 23 is configured to trigger alarms if the actual pressure drop and/or the transmembrane pressure and/or the access transmembrane pressure is/are outside respective safe range/s.

The illustrated example of FIG. 1 shows pressure drops due tube sections and to the blood warming bag 17 of the blood warming device 1. Anyway, pressure drops may be due to other devices on the extracorporeal blood circuit 6, 7, e.g. a gas exchanger, hemoperfusion device or others.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the scope of the appended claims.

The invention claimed is:

1. Extracorporeal blood treatment apparatus, comprising:
   a blood treatment device;
   an extracorporeal blood circuit coupled to the blood treatment device and comprising a blood withdrawal line connected to a blood inlet port of the blood treatment device and blood return line connected to a blood outlet port of the blood treatment device;
   a blood pump, wherein a pump section of the extracorporeal blood circuit is configured to be coupled to the blood pump;
   a first pressure sensor located in a first measurement site on the on the blood withdrawal line upstream of the blood treatment device;
   a second pressure sensor located in a second measurement site on the blood return line downstream of the blood treatment device;
   an electronic control unit operatively connected to the first pressure sensor and to the second pressure sensor, wherein the electronic control unit is configured to:
   receive, from the first pressure sensor, a signal correlated to a measured blood pressure in the first measurement site;
   receive, from the second pressure sensor, a signal correlated to a measured blood pressure in the second measurement site; and
   correct the measured blood pressure of at least one of:
     the first pressure sensor through a mathematical correction model to obtain an actual blood pressure in a first reference site other than the first measurement site, wherein a first circuit section is positioned between the first reference site and the first measurement site, and the mathematical correction model is a model of at least one pressure drop in the first circuit section; and
     the second pressure sensor through a mathematical correction model to obtain an actual blood pressure in a second reference site other than the second measurement site, wherein a second circuit section is positioned between the second reference site and the second measurement site, and the mathematical correction model is a model of at least one pressure drop in the second circuit section.

2. Apparatus according to claim 1, wherein between the first reference site and the first measurement site, a first additional device is positioned, wherein determining a pressure drop is achieved through a mathematical correction model of a pressure drop in the first circuit section and in the first additional device.

3. Apparatus according to claim 2, wherein the first additional device comprises one or more of the blood pump, a drip chamber, and line connectors.

4. Apparatus according to claim 1, wherein between the second reference site and the second measurement site, a second additional device is positioned, wherein determining a pressure drop is achieved through a mathematical correction model of a pressure drop in the second circuit section and in the second additional device.

5. Apparatus according to claim 4, wherein the second additional device comprises one or more of a blood warming device, a gas exchanger, line connectors, a drip chamber, and an additional blood treatment device.

6. Apparatus according to claim 1, wherein the first measurement site is at the blood inlet port of the blood treatment device and the second measurement site is at the blood outlet port of the blood treatment device.

7. Apparatus according to claim 1, wherein the electronic control unit is configured to calculate an actual pressure drop of the blood treatment device as a difference between the actual blood pressure in the first reference site and the actual blood pressure in the second reference site.

8. Apparatus according to claim 1, wherein the blood treatment device comprises a blood chamber and a fluid chamber separated from one another by a semipermeable membrane, the apparatus further comprising:
- a treatment fluid circuit including an effluent line connected with a fluid outlet port of the fluid chamber and configured to receive a filtered waste fluid through the semipermeable membrane, and
- an effluent pressure sensor placed on the effluent line;
wherein the blood chamber comprises the blood inlet port and the blood outlet port and the electronic control unit is configured to:
- receive, from the effluent pressure sensor, a signal correlated to a filtered waste fluid pressure,
- calculate an actual access trans-membrane pressure of the blood treatment device as a difference between the actual blood pressure in the first reference site and the filtered waste fluid pressure.

9. Apparatus according to claim 8, wherein the electronic control unit is configured to calculate an actual trans-membrane pressure of the blood treatment device through the formula:

$$TMP_{actual} = \left(\frac{(P_{inlet} - P_{outlet})}{2}\right) - P_{effluent}$$

wherein
$TNP_{actual}$ is the actual trans-membrane pressure of the blood treatment device;
$P_{inlet}$ is the actual blood pressure in the first reference site;
$P_{outlet}$ is the actual blood pressure in the second reference site; and
$P_{effluent}$ is the filtered waste fluid pressure.

10. Apparatus according to claim 1, comprising a deaeration chamber placed on the blood return line, wherein the second pressure sensor is positioned at the deaeration chamber.

11. Apparatus according to claim 1, wherein the first reference site is closer to the blood treatment device than the first measurement site and the second reference site is closer to the blood treatment device than the second measurement site.

12. Apparatus according to claim 1, wherein the electronic control unit is configured to calculate a trans-membrane pressure of the blood treatment device as a function of the actual blood pressure in the first reference site and/or in the second reference site.

13. Apparatus according to claim 1, wherein the electronic control unit is configured to process the signal correlated to the measured pressure of the blood in the first measurement site to obtain a mean value of the blood pressure in the first measurement site and to process the signal correlated to the measured pressure of the blood in the second measurement site to obtain a mean value of the blood pressure in the second measurement site.

14. Apparatus according to claim 1, wherein the electronic control unit is connected to the blood pump and is configured to:
- operate the blood pump to generate a variable blood flow comprising a constant flow component of a desired blood flow value and a variable flow component having a nil mean value, the variable blood flow generating at least in the first measurement site and in the second measurement site a pressure progression that is variable in time comprising a pressure component oscillating about a mean value;
- receive from the first pressure sensor a plurality of pressure values for a time period comprising a plurality of pressure oscillations about the mean value, the pressure values being measured at successive time instants;
- receive from the second pressure sensor a plurality of pressure values for a time period comprising a plurality of pressure oscillations about the mean value, the pressure values being measured at successive time instants;
- determine the pressure drop of the mean value of the measured pressure between the first measurement site and the first reference site;
- determine the pressure drop of the mean value of the measured pressure between the second measurement site and the second reference site;
- correct the mean value of the measured pressure at the first measurement site using the mathematical correction model; and
- correct the mean value of the measured pressure at the second measurement site using the mathematical correction model.

15. Apparatus according to claim 1, wherein the mathematical correction model is a function of blood flow rate and a first section geometry in the first circuit section and a second section geometry in the second circuit section.

16. Apparatus according to claim 1, wherein the mathematical correction model is a function of blood flow rate and one of kinematic viscosity or dynamic viscosity of the blood flowing in the first circuit section and one of kinematic viscosity or dynamic viscosity of the blood flowing in the second circuit section.

17. Apparatus according to claim 16, wherein the kinematic viscosity or the dynamic viscosity is estimated through blood temperature and blood protein concentration respectively in the first circuit section and in the second circuit section.

18. Apparatus according to claim 1, wherein the mathematical correction model is an empirical model of a measurement error derived from a plurality of experimental data sets, the measurement error being a difference between the blood measured pressure in the measurement site and the blood actual pressure in the reference site, the mathematical correction model being derived from a regression analysis of the measurement error collected through said plurality of experimental data sets versus one or more parameters including the blood flow rate collected through said plurality of experimental data sets.

19. An extracorporeal blood treatment apparatus, comprising:
a blood treatment device comprising a blood chamber and a fluid chamber separated from one another by a semipermeable membrane;
an extracorporeal blood circuit coupled to the blood treatment device and comprising a blood withdrawal line connected to a blood inlet port of the blood chamber of the blood treatment device and blood return line connected to a blood outlet port of the blood chamber of the blood treatment device;
a blood pump, wherein a pump section of the extracorporeal blood circuit is configured to be coupled to the blood pump;
a treatment fluid circuit operatively connected to the extracorporeal blood circuit and comprising an effluent line connected with the fluid outlet port of the fluid chamber to receive a filtered waste fluid through the semipermeable membrane;
at least one pressure sensor located at a measurement site on the extracorporeal blood circuit;
an electronic control unit operatively connected at least to the pressure sensor and configured to:
receive, from the pressure sensor, a signal correlated to a measured pressure in the measurement site;
determine a pressure drop between the measurement site and a reference site other than the measurement site, the reference site being a site on the extracorporeal blood circuit, wherein between the reference site and the measurement site, a circuit section and at least one additional device are positioned; and
correct the measured pressure in the measurement site based on the determined pressure drop to obtain an actual blood pressure at the reference site.

20. Apparatus according to previous claim 19, wherein the electronic control unit is configured to determine a pressure drop using a mathematical correction model of a pressure drop in the circuit section and in the additional device.

21. Apparatus according to claim 19, wherein said at least one pressure sensor comprises a first pressure sensor located on the blood withdrawal line upstream of the blood treatment device, wherein the electronic control unit is configured to:
receive, from the first pressure sensor, a signal correlated to a first measured blood pressure upstream the blood treatment device;
correct the first measured blood pressure using a first mathematical correction model to obtain an actual first blood pressure at the blood inlet port of the blood treatment device.

22. Apparatus according to claim 21, wherein said at least one pressure sensor comprises a second pressure sensor located on the blood return line downstream of the blood treatment device, wherein the electronic control unit is configured to:
receive, from the second pressure sensor, a signal correlated to a second measured blood pressure downstream the blood treatment device;
correct the second blood measured pressure using a second mathematical correction model to obtain an actual second blood pressure at the blood outlet port of the blood treatment device.

23. Apparatus according to claim 22, wherein the electronic control unit is configured to calculate an actual pressure drop of the blood treatment device as a difference between the actual first blood pressure and the actual second blood pressure.

24. Apparatus according to claim 19, comprising an effluent pressure sensor placed on the effluent line,
wherein the electronic control unit is configured to:
receive, from the effluent pressure sensor, a signal correlated to a filtered waste fluid pressure,
calculate an actual access trans-membrane pressure of the blood treatment device as a difference between the actual blood pressure at the reference site and the filtered waste fluid pressure.

25. Apparatus according to claim 19, wherein said at least one additional device comprises one or more of a blood warming device, a gas exchanger, line connectors, a drip chamber, and an additional blood treatment device.

26. Apparatus according to claim 19, comprising a deaeration chamber placed on the blood return line, wherein the pressure sensor is positioned at the deaeration chamber and said at least one additional device is placed on the blood return line between the blood treatment device and the deaeration chamber, the reference site being at the blood outlet port of the blood treatment device.

27. Apparatus according to claim 19, wherein the electronic control unit is configured to calculate a trans-membrane pressure of the blood treatment device as a function of a mean value of the measured blood pressure in the measurement site and the determined pressure drop between the measurement site and the reference site.

28. Apparatus according to claim 19, wherein the apparatus comprises an auxiliary pressure sensor located on an auxiliary measurement site either in the extracorporeal blood treatment or in the treatment fluid circuit, wherein the electronic control unit is configured to:
receive from the auxiliary pressure sensor a signal correlated to a measured auxiliary pressure in the auxiliary measurement site;
correct the auxiliary measured pressure using an auxiliary mathematical correction model to obtain an actual auxiliary pressure in an auxiliary reference site other than the auxiliary measurement site, the auxiliary reference site being on the extracorporeal blood circuit or on the treatment fluid circuit, wherein an auxiliary circuit section is positioned between the auxiliary reference site and the auxiliary measurement site, wherein the auxiliary mathematical correction model is a model of at least an auxiliary pressure drop in the auxiliary circuit section;
determine an auxiliary pressure drop between the auxiliary measurement site and the auxiliary reference site; and
calculate a trans-membrane pressure of the blood treatment device as a function of:
the actual blood pressure in the reference site; and
either the actual auxiliary pressure in the auxiliary reference site, or the measured auxiliary pressure in the auxiliary measurement site.

29. Apparatus according to claim 28, wherein the pressure sensor is located on the blood withdrawal line or on the blood return line and the auxiliary pressure sensor is located on the other of the blood withdrawal line and the blood return line.

30. Apparatus according to claim 28, wherein the pressure sensor is located on the blood withdrawal line or on the blood return line and the auxiliary pressure sensor is located on the treatment fluid circuit.

31. Apparatus according to claim 28, wherein the auxiliary reference site is a reference site located at a venous drip chamber on the blood return line.

\* \* \* \* \*